United States Patent [19]

Teirstein

[11] Patent Number: 5,533,978
[45] Date of Patent: Jul. 9, 1996

[54] METHOD AND APPARATUS FOR UNINTERRUPTED DELIVERY OF RADIOGRAPHIC DYE

[76] Inventor: Paul S. Teirstein, 402 Coast Blvd., South, La Jolla, Calif. 92037

[21] Appl. No.: 336,252

[22] Filed: Nov. 7, 1994

[51] Int. Cl.⁶ ............................................. A61M 5/178
[52] U.S. Cl. .................. 604/183; 604/53; 604/80; 604/125; 604/247
[58] Field of Search .................. 604/48, 49, 65, 604/52, 53, 80–83, 89, 127, 122–125, 128, 181, 151–153, 183, 186, 187, 191, 212, 213, 207, 215, 247, 254, 255–258, 403, 407, 408, 410, 129; 137/574, 578, 613, 558, 565, 568, 254, 44, 54

[56] References Cited

U.S. PATENT DOCUMENTS

| | | |
|---|---|---|
| 3,287,721 | 11/1966 | Baehr . |
| 4,014,010 | 3/1977 | Jinotti . |
| 4,078,563 | 3/1978 | Tuseth ..................... 604/127 |
| 4,319,568 | 3/1982 | Tregoning . |
| 4,496,346 | 1/1985 | Mosteller . |
| 4,695,271 | 9/1987 | Goethel . |
| 4,764,166 | 8/1988 | Spani ........................................ 604/65 |
| 5,334,170 | 8/1994 | Moroski ................................... 604/80 |
| 5,423,751 | 6/1995 | Harrison et al. ......................... 604/83 |

Primary Examiner—John D. Yasko
Assistant Examiner—Ronald K. Stright, Jr.
Attorney, Agent, or Firm—Gerald W. Spinks

[57] ABSTRACT

A method and apparatus for injecting radiographic dye during angiography are provided. A deformable holding chamber is interposed between a contrast dye bottle and a syringe manifold. A one-way valve and an integral disconnect/flow-stop are connected between the bottle and the holding chamber. A vent is provided in the holding chamber, with a second one-way valve. Squeezing and releasing the deformable chamber fills the chamber from the bottle. The holding chamber contains a floating baffle which acts as a shut off valve by plugging the chamber outlet if the chamber becomes empty. The syringe is used to withdraw dye from the holding chamber. If dye remains in the bottle after performance of the procedure, the disconnect/flow-stop fitting can be disconnected, and the dye can be saved.

13 Claims, 2 Drawing Sheets

METHOD AND APPARATUS FOR UNINTERRUPTED DELIVERY OF RADIOGRAPHIC DYE

FIELD OF INVENTION

This invention is in the field of angiography using a liquid contrast dye.

BACKGROUND OF THE INVENTION

A procedure commonly performed is the catheterization of the cardiovascular system of a patient, requiring the performance of angiography to assist the physician in visualizing the catheter and other instruments within the blood vessels. Typical of procedures for which catheterization is performed are atherectomy and angioplasty procedures. During angiography, a radiopaque contrast dye or other medium is usually injected into the vascular system to render the lumen of the vessel visible via radiographic equipment.

The contrast dye is typically provided in containers such as bottles with puncturable receptacles. The receptacle is punctured with a spike, which can be vented, and the spike is typically connected to the proximal end of a flexible tube. The bottle is hung from a stand to provide a hydrostatic head, and the distal end of the flexible tube can be connected to a manifold or other valving device. The manifold is also connected to a syringe and to the proximal end of a guide catheter, the distal end of which is inserted into the vascular system of the patient.

During the catheterization procedure, when the physician wishes to inject dye into the blood vessel, the plunger of the syringe is first withdrawn, with the manifold or other valves aligned as required to allow flow of dye from the contrast bottle, through the tubing and the manifold, to the syringe. The manifold valves are then realigned as necessary, to allow flow from the syringe to the guide catheter, and the plunger is pushed into the syringe to dispense contrast dye into the patient's vascular system, through the manifold and the guide catheter. After the syringe is emptied, if another dye injection is required, the physician again draws dye from the bottle into the syringe and dispenses the dye into the guide catheter.

Two problems can result from this conventional method of dye injection. First, the method is unnecessarily expensive, because it wastes large amounts of very expensive contrast dye. Each cardiovascular catheterization procedure typically only requires about 70 or 80 milliliters of contrast dye. After performance of the typical procedure, some of the contrast dye usually will be left in the bottle. This remaining dye can not be used in a subsequent procedure on another patient, because of the risk of contamination. In other words, contaminated fluids from the first patient might, conceivably, flow back through the syringe to the contrast bottle, subsequently contaminating the second patient. To guard against this possibility, the contrast dye remaining in a bottle typically is discarded. If large bottles are used, a large amount of dye can be wasted. Considering that the contrast material costs approximately one dollar per milliliter, this practice results in substantial unnecessary expense.

Secondly, when the physician repeatedly fills the syringe, if the contrast bottle approaches empty, air will eventually be drawn into the tubing and possibly into the syringe. This requires stopping the catheterization procedure while a new bottle of fluid is attached, and while the air is purged from the syringe and the tubing. If smaller bottles are used to limit waste, additional time in surgery can be required for repeatedly changing bottles and repriming the flowpath. Given the invasive nature of cardiac catheterization in particular, and given the fact that blood flow in the affected vessel is substantially reduced during the procedure, any delay in the procedure is very undesirable.

It is an object of the present invention, then, to provide a method and apparatus for injecting radiographic dye into a vascular system, which will allow the use of essentially all of the contrast material in a bottle before discarding the bottle, without fear of contamination. It is a further object of the present invention to provide a method and apparatus for injecting radiographic dye into a vascular system, which will allow the replacement of an empty contrast bottle with a replacement bottle, without stopping the procedure. Finally, it is an object of the present invention to provide a method and apparatus for injecting radiographic dye into a vascular system, which is easy and economical to implement.

SUMMARY OF THE INVENTION

A preferred embodiment of the present invention, for illustrative purposes only, includes a method and apparatus for injecting radiographic dye during cardiovascular catheterization that interposes a deformable holding chamber between the contrast bottle and the syringe manifold. Flow control devices are installed to allow rapid filling of the holding chamber, replacement of an empty bottle with a full bottle without interrupting the procedure, and separation of the holding chamber from a partially emptied contrast bottle to permit use of the remainder of the contrast dye in a subsequent procedure. A tube is connected between the vented spike in the contrast bottle and the holding chamber, with two flow control devices installed at intermediate positions along the tube. A floating baffle of latex or some other impermeable membrane, stretched across a floating frame, is contained within the holding chamber. As the level of dye in the holding chamber reaches the bottom of the chamber, the impermeable membrane covers and plugs the chamber outlet to prevent air from entering the outlet line from the holding chamber.

The first flow control device in the tube between the vented spike and the holding chamber is a disconnect fitting with an integral automatic flow-stop. The fitting is a device available on the market, which has two halves joined by mating threads. Each half of the fitting is connected to the tubing so as to cause all flow through the tubing to flow through the fitting. Disconnection of the fitting, thereby disconnecting the tubing, is accomplished by separating the two halves of the fitting at the threads. The upstream half of the fitting, connected to the tubing leading from the contrast bottle, contains an integral automatic flow-stop. When the two halves of the fitting are separated at the threads, the flow-stop automatically closes, preventing flow through the upper half of the fitting.

The second flow control device is a one way valve which is installed to allow flow only from the contrast bottle into the holding chamber. The one way valve can be one of a number of such devices available on the market. It should be suitable for preventing even low flow rates in the reverse direction. This device is installed in the tubing between the disconnect/flow-stop fitting and the holding chamber. Therefore, the one way valve prevents flow of fluid from the holding chamber back to the contrast bottle while the tubing is still connected, and it prevents flow of fluid out of the holding chamber to the atmosphere after the tubing is disconnected.

A third device which can optionally be installed on the tubing between the contrast bottle and the holding chamber is an air-in-line sensor, which can be one of several available on the market. It can, for instance, be ultrasonically operated, or based on infrared or photoelectric technology. This sensor can detect air or other gas in the tubing, such as an air bubble which might enter the tubing if the contrast bottle empties unnoticed by the physician. When air is sensed by this sensor, an alarm is sounded, and the contrast bottle can be replaced with a full bottle before air enters the tubing leading to the syringe manifold. This obviates the need to stop the procedure, since contrast medium will still be available in the holding chamber for any injections that are needed during bottle replacement. This can also facilitate the removal of air from the tubing after replacement of the contrast bottle, since as will be seen, repriming of the holding chamber will automatically remove the entrapped air from the tubing upstream of the holding chamber. As an alternative, the air sensor can be installed on the outside of the holding chamber at a selected level to warn that the level of dye in the chamber is falling. The selected level would be below the normal full level but above the empty level to insure that several injections are still available while the dye bottle is being exchanged.

The deformable chamber is also fitted with a pierceable seal and a vent opening. The pierceable seal allows secondary injections or connections as desired. The vent opening is fitted with a second one way valve, which can be operated by a low pressure differential, like the first one way valve, or it can be a high pressure crack valve which opens only upon seeing a relatively high pressure differential across the valve. The second one way valve is oriented to allow flow only out of the holding chamber to the atmosphere. If desired, a manual stop valve can be installed in the vent line between the second one way valve and the holding chamber. The manual stop valve is required only if the one way valve in the vent is a typical one way valve having a relatively low cracking pressure. If the second one way valve is a high pressure crack valve, the manual valve is not needed.

In order to use the apparatus of the present invention, the vented spike is inserted into the receptacle on the contrast bottle, and the bottle is hung on a stand. If installed, the manual stop valve on the holding chamber vent is opened. Then, the deformable holding chamber is squeezed and released one or more times, to expel air out the chamber vent and draw contrast dye into the chamber from the contrast bottle. This process is repeated until the holding chamber contains the desired amount of dye, preferably about 30 milliliters. Then, the manual valve on the holding chamber vent is closed, if one is installed. Partial filling of the holding chamber leaves an air space in the chamber, which acts as a contamination barrier when combined with the presence of the first one way valve in the inlet tube.

The presence of the vent on the holding chamber allows the holding chamber to be filled much more rapidly than if the venting of the apparatus were to be done entirely through the dye bottle, as was seen in the prior art device. Moreover, the presence of the second one way valve in the vent line promotes the rapid filling of the holding chamber. Squeezing the holding chamber forces air out the vent through the second one way valve. When the holding chamber is released and allowed to expand to its original size, the second one way valve prevents air from flowing back into the holding chamber through the vent. This ensures the formation of a vacuum in the holding chamber to draw dye into the chamber from the dye bottle, via the first one way valve.

When the physician wishes to inject dye into the patient, the manifold valves are aligned to allow flow from the holding chamber into the syringe. Then, the syringe plunger is withdrawn to draw dye from the holding chamber into the syringe. As dye is drawn into the syringe from the holding chamber, replacement dye is drawn into the holding chamber from the contrast bottle. The manifold valves are then aligned to allow flow from the syringe into the guide catheter, and the plunger is pushed into the syringe to dispense dye into the patient.

If the procedure is completed without using all of the dye in the contrast bottle, the battle can be removed and saved for another procedure by disconnecting the disconnect/flow-stop fitting. The equipment downstream from the fitting, including the lower half of the fitting, can be discarded. The equipment upstream of the fitting is safe to save, since the interposition of the holding chamber and the one way valve between the disconnect/flow-stop fitting and the patient insures that no contamination can reach the fitting.

If the contrast material in the bottle is exhausted before the procedure is complete, the bottle can be removed by removing the spike from the bottle and inserting it into a new bottle. After a replacement bottle is connected, the holding chamber and the tubing from the contrast bottle can be reprimed by squeezing and releasing the holding chamber as before, if required.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF PREFERRED EMBODIMENTS

Figure 1:
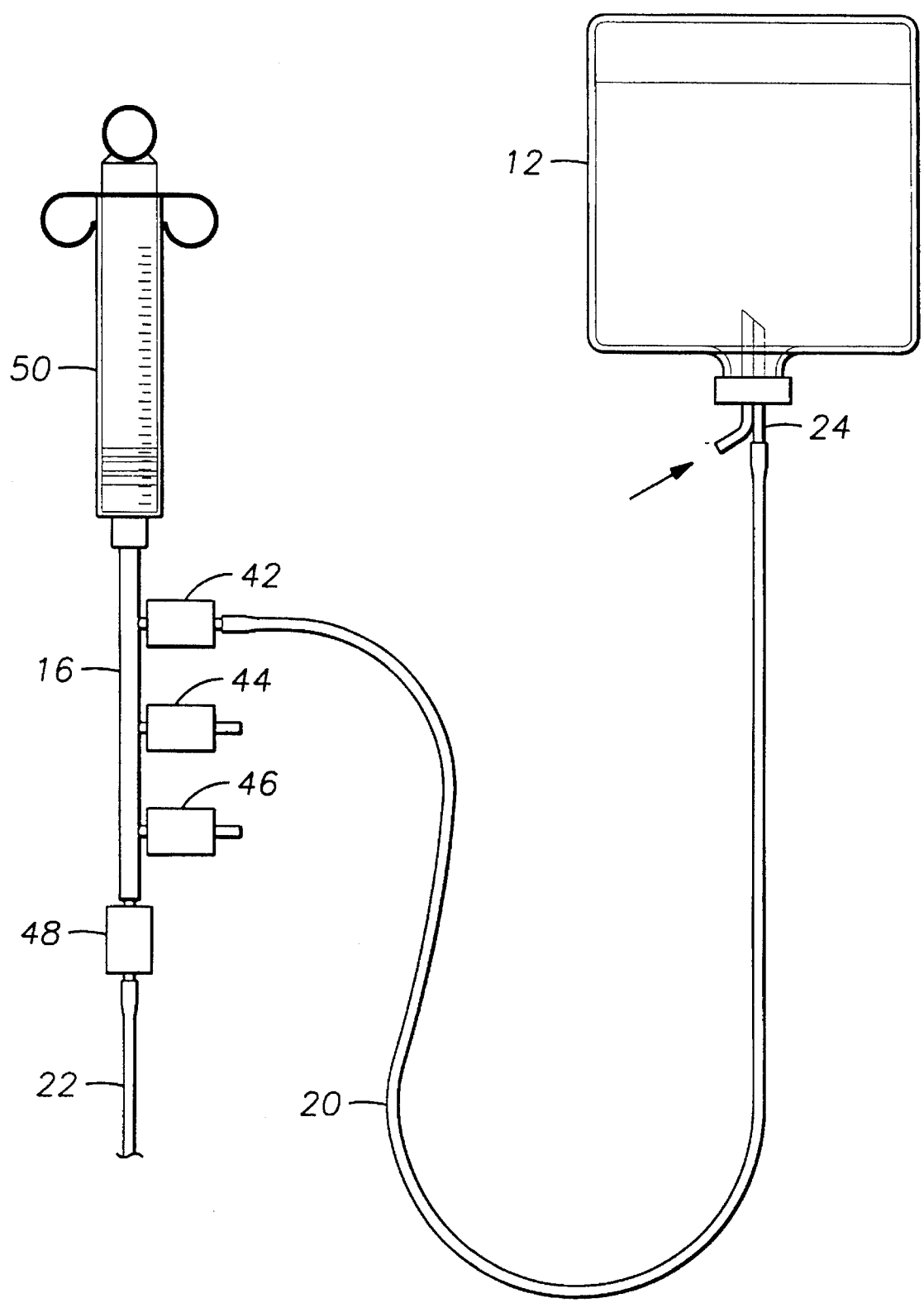
FIG. 1 is a schematic diagram of a typical dye injection apparatus as is known in the art.

As seen in FIG. 1, a typical dye injection apparatus as is known in the art includes three basic components. Specifically, they are a contrast dye bottle 12, a dye manifold 16, and a syringe 50. The contrast bottle 12 is connected to the manifold 16 by a vented spike 24 and a length of tubing 20. The manifold 16 is also connected to a branch of a guide catheter (not shown) by a second length of tubing 22.

The vented spike 24 is inserted into the bottle 12 via a receptacle in the mouth of the bottle 12. As fluid is drawn from the bottle 12, air is drawn into the bottle 12 through the branch of the spike 24, as shown by the arrow. The fluid conduit of the spike 24 is connected to the proximal end of the flexible tubing 20. The distal end of the tubing 20 is connected to an inlet valve 42 on the manifold 16. Typically, a manifold 16 will also have other valves 44, 46, as well as an outlet valve 48. A proximal end of the second tubing 22 is connected to the outlet valve 48. Finally, the syringe 50 is connected to the manifold 16. The manifold 16 could have various types of valves, including manual valves or check valves, to control the flow of the contrast dye. Indeed, the manifold 16 could be replaced by a multi-ported ball valve. However, the functioning of the apparatus can be most easily illustrated by discussion of a manifold 16 having manual valves as shown.

Once connected as shown, the known apparatus must be primed by drawing dye into the syringe and dispensing it into the guide catheter, including the purging of all air bubbles from the manifold 16 and the tubing 20. This is a time consuming operation. When it is desired to inject contrast dye into the patient, the physician withdraws the plunger of the syringe 50, with inlet valve 42 open and outlet valve 48 closed. When the syringe 50 is filled with dye, inlet valve 42 is shut and outlet valve 48 is opened. Then, the plunger is inserted back into the syringe 50, dispensing the dye through the manifold 16, and through the tubing 22, to the guide catheter. Each injection will typically dispense approximately 7 ml. of dye. Repeated injections are repeated as required. After the angiography procedure has been completed, approximately half of the dye in bottle 12 will remain. The entire apparatus, including the remaining dye, must be discarded, since there is no assurance that contaminated fluid has not migrated back up through the apparatus into the bottle 12.

Figure 2:
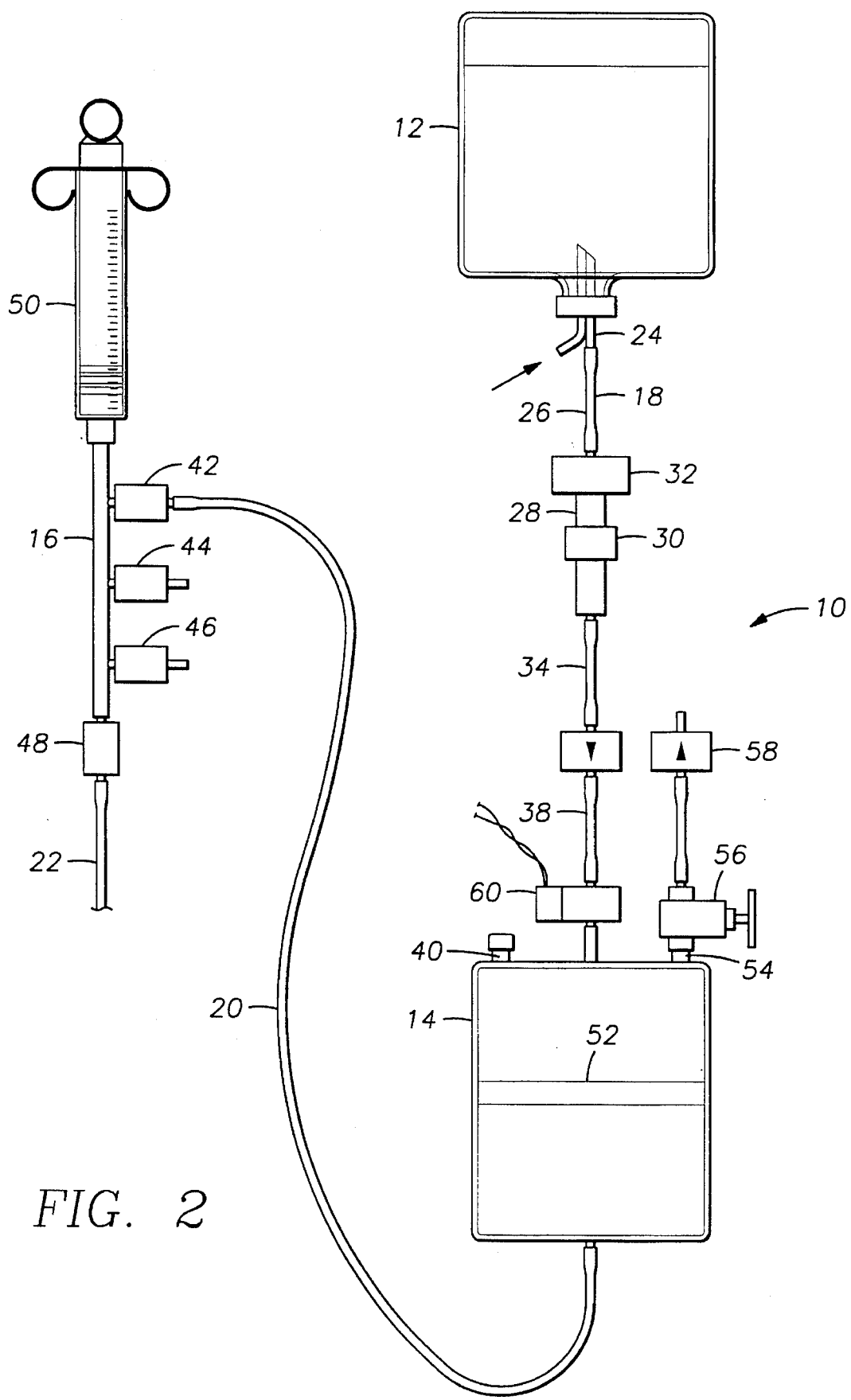
FIG. 2 is a schematic diagram of the dye injection apparatus of the present invention.

FIG. 2 shows a preferred embodiment of the apparatus of the present invention 10. The contrast bottle 12 is ultimately connected, as before, to the manifold 16 and the syringe 50. In this case, however, apparatus is interposed between the bottle 12 and the manifold 16 to ensure that contamination does not migrate back to the bottle 12, and to facilitate disconnection of the bottle 12 from the other apparatus, to allow saving the remaining dye in the bottle 12, or to allow replacement of an empty bottle with a full bottle.

The intervening apparatus consists of a deformable holding chamber 14, which is connected to the bottle 12 by several additional components in a flow path 18. Connected to the fluid conduit of spike 24 is the proximal end of a length of tubing 26, forming a portion of the flow path 18. Continuing along flow path 18, the distal end of the tubing 26 is connected to the proximal end of a disconnect/flow-stop fitting 28. The disconnect/flow-stop fitting 28 consists essentially of two portions, a flow-stop portion 32 and a threaded disconnect portion 30. The fitting 28 can be one of a number of such fittings available on the market. When the threaded disconnect portion 30 is disconnected, thereby breaking the flow path 18, the integral flow-stop portion 32 automatically stops flow through the flow path 18 from the bottle 12.

The distal end of the fitting 28 is connected to the proximal end of a second length of tubing 34, the distal end of which is connected to the proximal end of a one-way valve 36. The one-way valve 36 allows flow only from the bottle 12 toward the holding chamber 14, as shown by the arrow. The one-way valve 36 can be one of a number of such valves available on the market. The distal end of the one-way valve 36 is connected to the proximal end of a third length of tubing 38, completing flow path 18. Indeed, the three lengths of tubing 26,34,38 can be seen to constitute essentially a single tubing with the disconnect fitting 28 and the one-way valve 36 interposed therebetween.

The tubing 38 can have attached thereon an air-in-line sensor, or bubble detector 60. The bubble detector 60 can be one of several such devices available on the market, which can operate on ultrasonic, photoelectric, or infrared technology. When a gas bubble is detected in the tubing 38, the sensor 60 will give an alarm signal to alert personnel to the need to replace the bottle 12 with a full bottle.

Alternatively, an air sensor 60' can be mounted on the holding chamber 14 to determine when the dye level has fallen below a selected level. Normally, the sensor 60' will be mounted at a level selected to be below the normal fill level in the chamber 14, but above the bottom of the chamber 14. Ideally, the level at which the sensor 60' is mounted will leave at least enough dye to supply several injections of dye after the air alarm is given. As dye is withdrawn from the holding chamber 14, a partial vacuum in the holding chamber 14 will draw additional dye from the bottle 12, causing the dye level in the holding chamber 14 to remain relatively constant. This means that the floating baffle 52 will normally remain above the level at which the sensor 60' is mounted, and the sensor 60' will not detect the presence of air. If the bottle 12 empties, repeated injections of dye into the patient will cause the baffle 52 to drop below the level of the sensor 60', and the air alarm will be energized.

An injection fitting 40 and a vent 54 are also mounted on the deformable chamber 14. The injection fitting 40 is fitted with a pierceable seal, allowing the injection of secondary fluids with a hypodermic needle, or allowing the connection of a secondary set of tubing as desired. The vent 54 is fitted with a stop valve 56 and a second one-way valve 58. The second one-way valve 58 is installed so as to allow flow only out of the holding chamber 14 to the atmosphere, as shown by the arrow. If the one-way valve 58 is a high pressure crack valve, the manual valve 56 is not needed.

The holding chamber 14 itself is a deformable chamber which is constructed so as to return to its original shape after being squeezed and released, with the resiliency being sufficient to draw dye out of the bottle 12 during return of the chamber 14 to its original shape. It should have visibility through at least a portion of its side wall, to allow personnel to see the level of dye therein. It should also have graduated markings on its side, and its capacity should be at least 30 ml. The baffle 52, such as a floating baffle, can be provided within the chamber 14, to prevent the entrainment of air in the dye by direct impingement of the stream of dye on the reservoir of dye in the bottom of the chamber 14. The baffle 52 consists of a floating frame and an impermeable membrane such as a latex membrane. As dye falls on top of the membrane, it flows around the outside of the frame, which loosely fits the inner diameter of the holding chamber 14. As the level of dye in the holding chamber 14 drops, the floating baffle 52 drops on top of the outlet of the chamber 14 and the impermeable membrane stops all flow out of the outlet.

OPERATION

With the apparatus 10 connected as shown in FIG. 2, and with contrast dye in the bottle 12, the vent valve 56 is opened. Then, the holding chamber 14 is squeezed and released several times to expel air from the holding chamber 14 through the vent 54, and to draw dye into the chamber 14 through the flow path 18. Filling of the chamber 14 is rapid because of the pumping effect of the deformable chamber 14, and because of the large capacity of the vent 54, as compared to venting only through the relatively small vented spike 24 as in the prior art. When the desired level of dye, typically about 30 ml., is in the holding chamber 14, the vent valve 56 is closed. This will leave an air gap in the top of the holding chamber 14.

When an injection is required, the plunger of the syringe 50 is withdrawn, with inlet valve 42 open and outlet valve 48 closed, and the dye is then dispensed by reinserting the plunger into the syringe 50, with the inlet valve 42 closed, and with the outlet valve 48 open. As mentioned before, these valves 42,48 could be check valves or a single multiport ball valve. As dye is withdrawn from the chamber 14 by the syringe 50, it is replaced by dye flowing from the bottle 12 to the chamber 14, because of the partial vacuum created in the chamber 14. Repeated injections can be accomplished by repeating the procedure as required.

If dye material is remaining in the contrast bottle 12 after the angiography is completed, the disconnect fitting 30 can be threadedly disconnected from the integral flow-stop 32, whereupon the integral flow-stop 32 will stop flow from the bottle 12. Alternatively, the spike connector 24 can be removed from the bottle 12, and a new spike connector 24 can be reinserted in the bottle 12 when the bottle 12 is used again. Since the patient has at all times been separated from the bottle 12 by an air gap in the holding chamber 14 and by the one-way valve 36, the dye remaining in the bottle 12 is sterile and can be used in a subsequent procedure.

If the bottle 12 becomes empty during the procedure, the bubble detector 60, 60' if installed, will warn attendants to replace the bottle 12 with a full bottle. Since there will be approximately 30 ml. of dye available in the chamber 14, there is ample time for the bottle to be replaced. After bottle replacement, the deformable chamber 14 can be repeatedly squeezed and released, with vent valve 56 open if present, to quickly return the level of dye in the chamber 14 to the desired level. This eliminates the need to purge air from the tubing 20, and repriming is accelerated by the deformability of the chamber 14. If the bubble detector 60, 60' is not installed, the holding chamber 14 affords an additional visible indication of the amount of dye remaining.

Further, flow path 18 includes a number of restricted passageways in the flow-stop 32 and in the one-way valve 36 which offer some resistance to liquid flow. Therefore, if the bottle 12 empties, followed by the emptying of the flow path 18, drawing of dye into the syringe 50 will become increasingly easy, because of the fact that air rather than liquid dye is being drawn through the flow path 18. This will offer the physician an additional indication that the bottle 12 is empty, while dye is still available in the chamber 14. If the dye level in the holding chamber 14 falls sufficiently, the baffle 52 will settle onto the outlet of the chamber 14 and act as a shut off valve to prevent air from entering the outlet line.

While the particular APPARATUS FOR UNINTERRUPTED DELIVERY OF RADIOGRAPHIC DYE as herein shown and disclosed in detail is fully capable of obtaining the objects and providing the advantages hereinbefore stated, it is to be understood that it is merely illustrative of the presently preferred embodiments of the invention and that no limitations are intended to the details of construction or design herein shown other than as described in the appended claims.

I claim:

1. A fluid delivery system, comprising:

a fluid reservoir, said fluid reservoir having an outlet;

a first air vent in fluid flow communication with said reservoir;

a deformable fluid holding chamber, said holding chamber having an inlet and an outlet;

a fluid shut off valve in said holding chamber for shutting off said outlet of said chamber when said chamber becomes empty;

a first tubular conduit connecting said outlet of said reservoir in flow communication with said inlet of said holding chamber;

a disconnect fitting connected in said first conduit between said outlet of said reservoir and said inlet of said holding chamber, said disconnect fitting having an integral automatic flow stop device for automatically stopping fluid flow out of said reservoir upon disconnection of said fitting;

a first one way valve connected in said first conduit between said disconnect fitting and said inlet of said holding chamber, said first one way valve permitting flow only from said reservoir to said holding chamber;

a second air vent in fluid flow communication with said holding chamber;

a second one way valve connected in fluid flow communication with said second air vent, said second one way valve permitting flow only from said holding chamber to the atmosphere;

a fluid manifold, said manifold having an inlet and an outlet;

a second tubular conduit connecting said outlet of said holding chamber in flow communication with said inlet of said manifold; and a fluid pumping device in fluid flow communication with said manifold for drawing fluid into said manifold through said manifold inlet, and for dispensing fluid from said manifold through said manifold outlet.

2. A fluid delivery system as claimed in claim 1, wherein said second one way valve is a high pressure crack valve.

3. A fluid delivery system as claimed in claim 1, wherein said shut off valve comprises a floating baffle mounted in said holding chamber for preventing air entrainment in the fluid, and for shutting off said chamber outlet.

4. A fluid delivery system as claimed in claim 1, further comprising a gas bubble detector mounted on said first conduit between said one way valve and said inlet of said holding chamber.

5. A fluid delivery system as claimed in claim 1, further comprising a gas bubble detector mounted on said holding chamber between said inlet and said outlet of said holding chamber.

6. A fluid delivery system as claimed in claim 1, wherein said fluid pumping device is a syringe.

7. A fluid delivery system, comprising:

a fluid reservoir, said fluid reservoir having an outlet;

a first air vent in fluid flow communication with said reservoir;

a deformable fluid holding chamber, said holding chamber having an inlet and an outlet;

a fluid shut off valve in said holding chamber for shutting off said outlet of said chamber when said chamber becomes empty;

a first tubular conduit connecting said outlet of said reservoir in flow communication with said inlet of said holding chamber;

a disconnect fitting connected in said first conduit between said outlet of said reservoir and said inlet of said holding chamber, said disconnect fitting having an integral automatic flow stop device for automatically stopping fluid flow out of said reservoir upon disconnection of said fitting;

a one way valve connected in said first conduit between said disconnect fitting and said inlet of said holding chamber, said one way valve permitting flow only from said reservoir to said holding chamber;

a fluid manifold, said manifold having an inlet and an outlet;

a second tubular conduit connecting said outlet of said holding chamber in flow communication with said inlet of said manifold;

a fluid pumping device in fluid flow communication with said manifold for drawing fluid into said manifold through said manifold inlet, and for dispensing fluid from said manifold through said manifold outlet;

a second air vent in fluid flow communication with said holding chamber; and a high pressure crack valve connected in fluid flow communication with said second air vent, said high pressure crack valve permitting flow only from said holding chamber to the atmosphere.

8. A fluid delivery system as claimed in claim 7, wherein said shut off valve comprises a floating baffle mounted in said holding chamber for preventing air entrainment in the fluid, and for shutting off said chamber outlet.

9. A fluid delivery system as claimed in claim 7, further comprising a gas bubble detector mounted on said first conduit between said first one way valve and said inlet of said holding chamber.

10. A fluid delivery system as claimed in claim 7, further comprising a gas bubble detector mounted on said holding chamber between said inlet and said outlet of said holding chamber.

11. A fluid delivery system as claimed in claim 7, wherein said fluid pumping device is a syringe.

12. A fluid delivery system, comprising:

a fluid reservoir, said fluid reservoir having an outlet;

a first air vent in fluid flow communication with said reservoir;

a deformable fluid holding chamber, said holding chamber having an inlet and an outlet;

a fluid baffle mounted in said holding chamber for preventing air entrainment in the fluid, and for shutting off said chamber outlet when said chamber becomes empty;

a first tubular conduit connecting said outlet of said reservoir in flow communication with said inlet of said holding chamber;

a disconnect fitting connected in said first conduit between said outlet of said reservoir and said inlet of said holding chamber, said disconnect fitting having an integral automatic flow stop device for automatically stopping fluid flow out of said reservoir upon disconnection of said fitting;

a one way valve connected in said first conduit between said disconnect fitting and said inlet of said holding chamber, said one way valve permitting flow only from said reservoir to said holding chamber;

a gas bubble detector mounted on said first conduit between said first one way valve and said inlet of said holding chamber;

a fluid manifold, said manifold having an inlet, an outlet, and a syringe port;

a second tubular conduit connecting said outlet of said holding chamber in flow communication with said inlet of said manifold;

a syringe connected in fluid flow communication with said syringe port for drawing fluid into said manifold through said manifold inlet, and for dispensing fluid from said manifold through said manifold outlet;

a second air vent in fluid flow communication with said holding chamber; and a high pressure crack valve connected in fluid flow communication with said second air vent, said high pressure crack valve permitting flow only from said holding chamber to the atmosphere.

13. A method of injecting radiographic dye into a vascular system of a patient, said method comprising the steps of:

providing a vented radiographic dye reservoir, a deformable dye holding chamber, a first line connecting said reservoir with said chamber, an integral disconnect with flow/stop in said first line, and a one way valve in said first line between said disconnect and said chamber, said one way valve allowing flow only from said reservoir to said chamber;

providing a fluid manifold connected to an outlet of said chamber by a second line, and a syringe connected to said fluid manifold for drawing dye into said manifold and for dispensing dye from said manifold;

providing a vent line attached to said chamber, with a high pressure crack valve connected to said vent line, said high pressure crack valve allowing flow only from said chamber to the atmosphere;

squeezing said chamber to expel air from said chamber to the atmosphere through said vent line and said high pressure crack valve;

releasing said chamber to allow said chamber to expand and draw dye from said, reservoir into said chamber, through said disconnect and said one way valve;

retracting a plunger from said syringe to draw dye from said chamber into said manifold;

inserting said plunger into said syringe to dispense dye from said manifold into a vascular system of the patient; and disconnecting said reservoir from said chamber by parting said first line at said disconnect, said integral flow/stop automatically stopping flow of dye from said reservoir through said first line, to allow use of dye remaining in said reservoir in a subsequent injection procedure.

\* \* \* \* \*